United States Patent [19]

Van Court Carr et al.

[11] Patent Number: 6,153,659
[45] Date of Patent: Nov. 28, 2000

[54] 3-{N-[2-(N',N'-DIMETHYLAMINO ETHOXY) ETHYL]-N-METHYLAMINO} PROPIONAMIDE FOR THE PRODUCTION OF POLYURETHANES

[75] Inventors: Richard Van Court Carr, Allentown; Ning Chen, Jamison; Mark Leo Listemann, Kutztown; Richard Paul Underwood, Allentown, all of Pa.

[73] Assignee: Air Products and Chemicals, Inc., Allentown, Pa.

[21] Appl. No.: 09/456,261

[22] Filed: Dec. 7, 1999

Related U.S. Application Data

[62] Division of application No. 09/276,966, Mar. 26, 1999, Pat. No. 6,037,496.
[51] Int. Cl.[7] .............................. C08J 9/08; C08G 18/18; C08G 18/20; C08G 18/24; C08G 18/32
[52] U.S. Cl. .......................... 521/115; 521/126; 521/129; 521/130; 521/163; 521/170
[58] Field of Search ....................................... 521/115, 126, 521/129, 130, 163, 170

[56] References Cited

U.S. PATENT DOCUMENTS

| | | | |
|---|---|---|---|
| 3,073,787 | 1/1963 | Krakler | 521/115 |
| 4,007,140 | 2/1977 | Ibbotson | 521/164 |
| 4,049,591 | 9/1977 | McEntire et al. | 521/129 |
| 4,094,827 | 6/1978 | McEntire | 521/129 |
| 4,194,069 | 3/1980 | Speranza et al. | 521/129 |
| 4,248,930 | 2/1981 | Haas et al. | 428/315 |
| 4,644,017 | 2/1987 | Haas et al. | 521/129 |
| 5,824,711 | 10/1998 | Kimock et al. | 521/129 |
| 5,874,483 | 2/1999 | Savoca et al. | 521/115 |
| 6,037,496 | 3/2000 | Carr et al. | 564/198 |

FOREIGN PATENT DOCUMENTS

| | | |
|---|---|---|
| 799821 | 10/1997 | European Pat. Off. . |
| 3027796 | 2/1982 | Germany . |

*Primary Examiner*—Rabon Sergent
*Attorney, Agent, or Firm*—Mary E. Bongiorno

[57] ABSTRACT

3-{N-[2-(N',N'-dimethylamino ethoxy)ethyl]-N-methylamino}propionamide is a new compound which is useful as a catalyst in the production of polyurethane foams.

3 Claims, No Drawings

3-{N-[2-(N',N'-DIMETHYLAMINO ETHOXY) ETHYL]-N-METHYLAMINO}PROPIONAMIDE FOR THE PRODUCTION OF POLYURETHANES

This is a division of application Ser. No. 09/276,966, filed on Mar. 26, 1999, now U.S. Pat. No. 6,037,496.

BACKGROUND OF THE INVENTION

Polyurethane foams are widely used in automotive, housing and other industries. The foams are produced through the reaction of a polyisocyanate with a polyol in the presence of various additives. One class of additives which is particularly effective as blowing agents is the chlorofluorocarbons (CFCs). CFCs vaporize as a result of the reaction exotherm during polymerization and cause the polymerizing mass to form a foam. However, the discovery that CFCs deplete ozone in the stratosphere has resulted in mandates for restricting CFC use. Therefore, more efforts have gone into the development of alternatives to CFCs for forming urethane foams and water blowing has emerged as an important alternative. In this method, blowing occurs from carbon dioxide generated by the reaction of water with the polyisocyanate. Foams can be formed by a one-shot method or by formation of a prepolymer and subsequent reaction of the prepolymer with water in the presence of a catalyst to form the foam. Regardless of the method, a balance is needed between reaction of the isocyanate and the polyol (gelling) and the reaction of the isocyanate with water (blowing) in order to produce a polyurethane foam in which the cells are relatively uniform and the foam has specific properties depending on the anticipated application; for example, rigid foams, semi-rigid foams, and flexible foams.

The ability of the catalyst to selectively promote either blowing or gelling is an important consideration in selecting a catalyst for the production of a polyurethane foam with specific properties. If a catalyst promotes the blowing reaction to too high a degree, carbon dioxide will be evolved before sufficient reaction of isocyanate with polyol has occurred. The carbon dioxide will bubble out of the formulation, resulting in collapse of the foam and production of a poor quality foam. At the opposite extreme, if a catalyst promotes the gelling reaction too strongly, a substantial portion of the carbon dioxide will be evolved after a significant degree of polymerization has occurred. Again, a poor quality foam is produced; characterized by high density, broken or poorly defined cells, or other undesirable features. Frequently, a gelling catalyst and a blowing catalyst are used together to achieve the desired balance of gelling and blowing in the foam.

Tertiary amine catalysts have been used in the production of polyurethanes. The tertiary amine catalysts accelerate both blowing (reaction of water with isocyanate to generate carbon dioxide) and gelling (reaction of polyol with isocyanate) and have been shown to be effective in balancing the blowing and gelling reactions to produce a desirable product. However, typical tertiary amines used as catalysts for polyurethane production generally have offensive odors and many are highly volatile due to low molecular weight. Release of tertiary amines during polyurethane production may present safety and toxicity problems, and release of residual amines from consumer products is generally undesirable.

Various alternatives to low molecular weight tertiary amine catalysts have been reported in the prior art. Examples are described below:

U.S. Pat. No. 3,073,787 (Krakler, 1963) discloses an improved process for preparing isocyanate foams in which a 3-dialkylaminopropionamide and 2-dialkylaminoacetamide are used as catalysts.

U.S. Pat. No. 4,007,140 (Ibbotson, 1977) discloses the use of various tertiary amines such as N,N'-bis(3-dimethylaminopropylamino)urea as low odor catalysts for the manufacture of polyurethanes.

U.S. Pat. No. 4,049,591 (McEntire et al., 1977) discloses a group of β-substituted bis (N,N-dimethylaminopropyl) amines as polyurethane catalysts. The substitution group can be cyano, amide, ester, or ketone.

U.S. Pat. No. 4,094,827 (McEntire, 1978) discloses the use of certain alkyl substituted ureas, such as N,N-bis (dimethylaminopropyl)urea, as catalysts in the production of polyurethane foam.

U.S. Pat. No. 4,194,069 (Speranza et al., 1980) discloses the use of N-(3-dimethylaminopropyl)-N'-(3-morpholinopropyl)urea as a catalyst for producing polyurethanes.

U.S. Pat. No. 4,248,930 (Haas et al., 1981) discloses new tertiary amine compounds, such as bis(dimethylamino-n-propyl)amine, as catalysts for the production of polyurethane resins.

U.S. Pat. No. 4,644,017 (Haas et al., 1987) discloses the use of diffusion stable amino alkyl ureas having tertiary amino groups in the production of a polyisocyanate addition product.

DE 3027796 (1982) (Derwent abstract 82-13914E) discloses the use of dialkyl aminoalkyl urea catalysts for the production of polyurethane foam. It is reported that no smell is generated at polyurethane preparation temperatures.

EP 799,821 (1997) discloses amine/amide catalysts, such as 3-[3-dimethyl-aminoproppyl]amino-N,N-dimethylpropanamide and 3-[3-dimethylaminopropyl] amino-N-[3-dimethylaminopropyl] propanamide, for formation of polyurethanes. The catalysts are reported to have low fugitivity due to their reactivity with isocyanates.

U.S. Pat. No. 5,824,711 (Kimock et al., 1998) discloses N,N,N'-trimethylbis-(aminoethyl)ether substituted urea compositions for the production of polyurethanes.

U.S. Pat. No. 5,874,483 (Savoca et al., 1999) discloses aminopropylbis(aminoethyl)ether compositions for the production of polyurethanes.

BRIEF SUMMARY OF THE INVENTION

This invention is directed to a new composition, 3-{N-[2-(N',N'-dimethylamino ethoxy)ethyl]-N-methylamino}propionamide, which is effective in catalyzing the reaction between an isocyanate and a compound containing a reactive hydrogen, such as an alcohol, a polyol, an amine or water. It is particularly effective in catalyzing the blowing reaction, i.e., the reaction between an isocyanate and water, in the production of foamed polyurethanes. The molecular structure of the new composition is shown below:

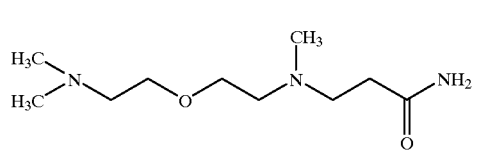

I

The advantages of the new compound in making polyurethane foams are:

its high catalytic activity;

its selectivity to the blowing reaction; and its capability to chemically bond to the urethane, thus preventing its release from the finished product.

DETAILED DESCRIPTION OF THE INVENTION

3-{N-[2-(N',N'-dimethylamino ethoxy)ethyl]-N-methylamino}propionamide is readily prepared by the nucleophilic addition of N,N,N'-trimethyl bis(aminoethyl) ether to an acrylamide. N,N,N'-trimethyl bis(aminoethyl) ether and acrylamide are present in the reaction mixture in molar ratio of from about 1:10 to about 20:1, and preferably at a ratio of 1 to 2 moles amine per equivalent of acrylamide. Air is used to saturate the reaction mixture in order to inhibit the free radical polymerization of acrylamide. The reaction is preferably carried out at atmospheric pressure; however other pressures can be used. The reaction can be carried out at a temperature from 0 and 100° C., preferably from 30 and 80° C., and is allowed to run for 0.1 to 100 hours, preferably from 2 to 6 hours.

In principle, the reagent monomer can be reacted in batch fashion, via staged addition, or continuously, whichever is most suitable. Synthesis is advantageously performed in a mixture of the neat monomers, however, an inert solvent for both reactants may be employed. Examples of suitable solvents include amides, halogenated hydrocarbons, esters, and ethers, preferred solvents are ethers.

The catalyst composition of this invention is selective to the blowing reaction for making foamed polyurethanes in which water reacts with an organic polyisocyanate to release carbon dioxide.

The polyurethanes are prepared using any suitable organic polyisocyanates well known in the art; for example, hexamethylene diisocyanate, phenylene diisocyanate, toluene diisocyanate ("TDI") and 4,4'-diphenylmethane diisocyanate ("MDI"). Especially suitable are the 2,4- and 2,6-TDI's individually or together as their commercially available mixtures. Other suitable isocyanates are mixtures of diisocyanates known commercially as "crude MDI", also known as PAPI, which contain about 60% of 4,4'-diphenylmethane diisocyanate along with other isomeric and analogous higher polyisocyanates. Also suitable are "prepolymers" of these polyisocyanates comprising a partially pre-reacted mixture of a polyisocyanate and a polyether or polyester polyol.

Illustrative of suitable polyols as a component of the polyurethane composition are the polyalkylene ether and polyester polyols. The polyalkylene ether polyols include the poly(alkylene oxide) polymers such as poly(ethylene oxide) and poly(propylene oxide) polymers and copolymers with terminal hydroxyl groups derived from polyhydric compounds, including diols and triols; for example, ethylene glycol, propylene glycol, 1, 3-butane diol, 1,4-butane diol, 1,6-hexane diol, neopentyl glycol, diethylene glycol, dipropylene glycol, pentaerythritol, glycerol, diglycerol, trimethylol propane and similar low molecular weight polyols.

In the practice of this invention, a single high molecular weight polyether polyol may be used. Also, mixtures of high molecular weight polyether polyols such as mixtures of di- and trifunctional materials and/or different molecular weight or different chemical composition materials may be used.

Useful polyester polyols include those produced by reacting a dicarboxylic acid with an excess of a diol, for example, adipic acid with ethylene glycol or butanediol, or reacting a lactone with an excess of a diol such as caprolactone with propylene glycol.

In addition to the polyether and polyester polyols, the masterbatch, or premix compositions, frequently contain a polymer polyol. Polymer polyols are used in polyurethane foam to increase the foam's resistance to deformation, i.e. to increase the load-bearing properties of the foam. Currently, two different types of polymer polyols are used to achieve load-bearing improvement. The first type, described as a graft polyol, consists of a triol in which vinyl monomers are graft copolymerized. Styrene and acrylonitrile are the usual monomers of choice. The second type, a polyurea modified polyol, is a polyol containing a polyurea dispersion formed by the reaction of a diamine and TDI. Since TDI is used in excess, some of the TDI may react with both the polyol and polyurea. This second type of polymer polyol has a variant called PIPA polyol which is formed by the in-situ polymerization of TDI and alkanolamine in the polyol. Depending on the load-bearing requirements for the polyurethane product, polymer polyols may comprise 20–80% of the polyol portion of the masterbatch.

Other typical agents found in the polyurethane foam formulations include chain extenders such as ethylene glycol and butanediol; crosslinkers such as diethanolamine, diisopropanolamine, triethanolamine and tripropanolamine; blowing agents such as water, methylene chloride, trichlorofluoromethane, and the like; and cell stabilizers such as silicones.

The amount of a catalyst composition which is effective in the formation of polyurethanes may range from about 0.01 to 10 parts per 100 parts polyol (phpp) in the polyurethane formulation. Preferred amounts range from about 0.05 to 0.5 phpp.

The 3-{N-[2-(N',N'-dimethylamino ethoxy)ethyl]-N-methylamino}-propionamide may be used in combination with other tertiary amine, organotin and carboxylate urethane catalysts well known in the urethane art. For example, suitable gelling catalysts include but are not limited to trimethylamine, triethylamine, tributyl-amine, trioctylamine, diethyl cyclohexylamine, N-methylmorpholine, N-ethylmorpholine, N-octadecylmorpholine (N-cocomorpholine), N-methyldiethanolamine, N,N-dimethylethanolamine, N,N'-bis(2-hydroxypropyl)piperazine, N,N,N',N'-tetramethylethylene-diamine, N,N,N',N'-tetramethyl-1,3-propanediamine, triethylenediamine (1,4-diaza-bicyclo [2.2.2]octane), 1,8-diazabicyclo(5.4.0)undecene-7, 1,4-bis (2-hydroxypropyl)-2-methylpiperazine, N,N'-dimethylbenzylamine, N,N-dimethylcyclohexylamine, benzyltriethylammonium bromide, bis(N,N-diethylaminoethyl)adipate, N,N-diethylbenzylamine, N-ethylhexamethyleneamine, N-ethylpiperidine, alpha-methylbenzyldimethylamine, dimethylhexadecylamine, dimethylcetylamine, and the like. Suitable blowing catalysts include but are not limited to bis(dimethylaminoethyl)ether, pentamethyldiethylenetriamine, 2-[N-(dimethylaminoethoxyethyl)-N-methylamino]ethanol, and the like.

A general polyurethane flexible foam formulation having a 1–3 lb/ft$^3$ (16–48 kg/m$^3$) density (e.g., automotive seating) containing a catalyst such as the catalyst composition according to the invention would comprise the following components:

| Component | Parts by Weight |
| --- | --- |
| Polyol | 20–100 |
| Polymer Polyol | 80–0 |
| Silicone Surfactant | 1–2.5 |
| Blowing Agent (e.g., water) | 2–4.5 |
| Crossslinker | 0.5–2 |
| Catalyst | 0.2–2 |
| Isocyanate Index | 70–115* |

*Isocyanate Index = (mole isocyanate/mole active hydrogen) × 100

The invention will be further clarified by a consideration of the following examples, which are intended to be purely exemplary of the invention.

EXAMPLE 1
Preparation of 3-{N-[2-(N',N'-dimethylamino ethoxy)ethyl]-N-methylamino}propionamide A 50 ml 3 neck round bottom flask was fitted with the following: magnetic stirrer, reflux condenser, air bubbler, and a temperature controlled oil bath. The flask was charged with 14.2 g of acrylamide. N,N,N'-trimethyl bis(aminoethyl) ether was added in one portion to the reaction flask at ambient temperature. After the addition, the reaction mixture was stirred at 75° C. for 6 hours. The mixture was cooled to ambient temperature. The resulting mixture was filtered through a Celite layer. The filtrate was collected for foam application. $^1$H NMR showed that the product was the desired structure.

EXAMPLE 2
Preparation of foam using 3-{N-[2-(N',N'-dimethylamino ethoxy)ethyl]-N-methylamino}propionamide Polyurethane foam was prepared in a conventional manner using the following premix formulation:

| Component | Parts by Weight |
| --- | --- |
| E-648 (ethylene oxide tipped polyether polyol, marketed by Arco) | 60 |
| E-519 (styrene-acrylonitrile copolymer filled polyether polyol, marketed by Arco) | 40 |
| Dabco ® DC-5043 surfactant (silicone surfactant marketed by Air Products and Chemicals, Inc.) | 1.5 |
| Diethanolamine | 1.75 |
| Water | 3.25 |
| TDI 80 (mixture of 80 wt. % 2,4-TDI and 20 wt. % 2,6-TDI) | 105* |

*Isocyanate Index

The catalyst was added to 202 g of the above premix in a 32 oz (951 ml) paper cup and the formulation was mixed for 20 seconds at 5000 RPM using an overhead stirrer fitted with a 2 inch (5.1 cm) diameter stirring paddle. Sufficient TDI 80 was added to make a 105 index foam [index=(mole isocyanate/mole active hydrogen)×100] and the formulation was mixed well for 5 seconds using the same overhead stirrer. The 32 oz. cup was dropped through a hole in the bottom of a 128 oz. (3804 ml) paper cup placed on a stand. The hole was sized to catch the lip of the 32 oz. cup. The total volume of the foam container was 160 oz. (4755 ml). Foams approximated this volume at the end of the foam forming process. Times to reach the top of the mixing cup (TOC1), the top of the 128 oz. cup (TOC2), and maximum foam height were recorded.

| Catalyst | TOC1 (sec.) | TOC2 (sec.) | Full Height (sec.) | Foam Height (mm) |
| --- | --- | --- | --- | --- |
| 0.25 pphp DABCO 33-LV$^a$/0.10 pphp DABCO BL-11$^b$ | 13.33 | 45.62 | 122.47 | 407.50 |
| 0.25 pphp DABCO 33-LV/0.23 pphp Example 1 catalyst | 13.39 | 46.30 | 123.27 | 409.86 |

$^a$DABCO 33-LV = 33 wt. % triethylene diamine in dipropylene glycol
$^b$DABCO BL-11 = 70 wt. % Bis(N,N-dimethylaminoethyl) ether in dipropylene glycol.

This example shows that 3-{N-[2-(N',N'-dimethylamino ethoxy)ethyl]-N-methylamino}propionamide is an effective blowing catalyst.

We claim:

1. A method for preparing polyurethane foam comprising reacting an organic polyisocyanate with a polyol in the presence of water and a catalyst composition comprising 3-{N-[2-(N',N'-dimethylamino ethoxy)ethyl]-N-methylamino}propionamide.

2. The method of claim 1 wherein the catalyst also comprises a tertiary amine, organotin or a carboxylate.

3. The method of claim 1 wherein the catalyst composition also comprises triethylenediamine.

* * * * *